(12) United States Patent
Terashi et al.

(10) Patent No.: US 10,603,471 B2
(45) Date of Patent: Mar. 31, 2020

(54) MEDICAL GUIDE WIRE

(71) Applicant: FMD Co., Ltd., Toda-shi, Saitama (JP)

(72) Inventors: Tsuyoshi Terashi, Toda (JP); Seiji Shimura, Toda (JP)

(73) Assignee: FMD Co., Ltd., Shibuya-ku, Tokyo (JP)

( * ) Notice: Subject to any disclaimer, the term of this patent is extended or adjusted under 35 U.S.C. 154(b) by 17 days.

(21) Appl. No.: 15/162,427

(22) Filed: May 23, 2016

(65) Prior Publication Data

US 2016/0346518 A1    Dec. 1, 2016

(30) Foreign Application Priority Data

May 29, 2015  (JP) ................. 2015-121514

(51) Int. Cl.
*A61M 25/09*    (2006.01)

(52) U.S. Cl.
CPC ... *A61M 25/09* (2013.01); *A61M 2025/09083* (2013.01); *A61M 2025/09175* (2013.01); *A61M 2210/12* (2013.01)

(58) Field of Classification Search
CPC ........ A61M 25/09; A61M 2025/09175; A61M 2025/09058; A61M 2025/09083
See application file for complete search history.

(56) References Cited

U.S. PATENT DOCUMENTS

| 5,345,945 | A * | 9/1994 | Hodgson ......... A61M 25/09033 600/433 |
| 2004/0122340 | A1* | 6/2004 | Vrba ..................... A61M 25/09 600/585 |
| 2008/0214959 | A1* | 9/2008 | Miyata ................. A61M 25/09 600/585 |
| 2010/0249654 | A1 | 9/2010 | Elsesser et al. |

(Continued)

FOREIGN PATENT DOCUMENTS

| EP | 2417998 A | 2/2012 |
| EP | 2689795 A | 1/2014 |

(Continued)

OTHER PUBLICATIONS

The extended European search report dated Oct. 19, 2016.
Japanese decision to grant a patent dated Feb. 16, 2016.
Japanese notice of the reason for refusal dated Oct. 27, 2015.

*Primary Examiner* — Devin B Henson
*Assistant Examiner* — H. Q. Nguyen
(74) *Attorney, Agent, or Firm* — Yokoi & Co., U.S.A.; Toshiyuki Yokoi

(57) ABSTRACT

In a guide wire of the present invention, a distal end portion of a core has a distal small-diameter body and a combined truncated cone including a first truncated cone in order from a distal end side to a proximal end side. A twist angle of the distal small-diameter body is specified to be larger than the twist angle of the first truncated cone to increase flexibility for easily bending at the distal end. At least one truncated cone is connected on the proximal end side of the first (Continued)

truncated cone to form the structure of a combined truncated cone. Thus, the guide wire of the present invention has high rotation transmission performance toward the distal end side and other performances. Accordingly, the guide wire can be quickly reached to the vascular lesion and has high passability at the vascular lesion.

5 Claims, 7 Drawing Sheets

(56) References Cited

U.S. PATENT DOCUMENTS

| | | | |
|---|---|---|---|
| 2011/0208092 A1* | 8/2011 | Nishigishi | A61M 25/09 600/585 |
| 2012/0041421 A1 | 2/2012 | Nishigishi | |
| 2012/0245488 A1 | 9/2012 | Matsumoto | |
| 2012/0265100 A1* | 10/2012 | Maki | A61M 25/09 600/585 |
| 2014/0276074 A1* | 9/2014 | Warner | F16C 1/02 600/459 |
| 2014/0358169 A1 | 12/2014 | Terashi et al. | |

FOREIGN PATENT DOCUMENTS

| | | |
|---|---|---|
| JP | 2001-009041 A | 1/2001 |
| JP | 4623906 B | 2/2011 |
| JP | 2012-005724 A | 1/2012 |
| JP | 2012-034922 A | 2/2012 |
| JP | 2012-200291 A | 10/2012 |
| JP | 2013-111320 A | 6/2013 |
| JP | 5565847 B | 8/2014 |
| JP | 2014-233411 A | 12/2014 |
| WO | 01/36034 A | 5/2001 |
| WO | 2009/039063 A | 3/2009 |

* cited by examiner

MEDICAL GUIDE WIRE

CROSS-REFERENCES TO RELATED APPLICATIONS

This patent specification is based on Japanese patent application, No. 2015-121514 filed on May 29, 2015 in the Japan Patent Office, the entire contents of which are incorporated by reference herein.

BACKGROUND OF THE INVENTION

1. Field of the Invention

The present invention relates to a medical guide wire used for treatment of a vascular lesion or the like.

2. Description of Related Art

Conventionally, in the treatment of the vascular lesion such as stenosis and occlusion at a peripheral part of a blood vessel, an operator sometimes performs a radial dilation (radial expansion) treatment on the occlusion by rotating a proximal end side (rear end side) of a medical guide wire (hereafter, referred to as a guide wire) and intentionally bends a distal end side of the guide wire in U-shape using a meandering portion of the blood vessel to reach the entrance of the vascular lesion, then pulling a little the proximal end side to restore the U-shape of the distal end to the original shape, and then making the guide wire pass through the occlusion of the blood vessel in order to avoid damaging the blood vessel wall at the peripheral part, prevent from entering in branches other than the vascular lesion, and finish the treatment immediately.

In the above described case, flexibility is required for easily bending and deforming the distal end side of the guide wire in U-shape, high rotation transmission performance from the proximal end side to the distal end side is required for making the guide wire pass through the occlusion of the blood vessel, and fatigue resistance is required for using repeatedly.

In Patent Document 1, a guide wire bent in U-shape (prolapse) at a distal end side is described.

In Patent Document 2, mechanical characteristic such as bending rigidity of a guide wire is described about a core located at the proximal end side rather than a coil spring located at the distal end side.

[Patent document 1] Japanese Patent Laid-Open Publication No. 2012-005724

[Patent document 2] Japanese Patent No. 4623906

BRIEF SUMMARY OF THE INVENTION

In the guide wire disclosed in Patent Document 1, the distal end of the core shaft (core) is separated from the most distal end part having an approximately semi-spherical shape, a flexible safety wire, the distal end of the core shaft and the coil body are connected with each other as a first brazing portion at the proximal end side compared to the most distal end part, and the guide wire is bent in U-shape (prolapse) using a rigidity difference between the distal end side and the proximal end side of the first brazing portion.

In the guide wire disclosed in Patent Document 2, the core is made of superelastic alloy of stainless steel or nickel-titanium, and bending rigidity is linearly changed in the longitudinal direction more significantly at the core located at the proximal end side than the coil spring located at the distal end portion. Thus, the operator does not feel rapid resistance and the operability can be improved.

Neither Patent document 1 nor 2 discloses the technology of the present invention. In the technology of the present invention, a distal end portion of the core in the coil includes a distal small-diameter body and at least one truncated cone, a preferable condition for bending the distal end portion in U-shape is found from a twist angle ratio between a twist angle of the distal small-diameter body and a twist angle of the truncated cone, and a combined truncated cone structure formed by connecting truncated cones is simultaneously used. Thus, the flexibility for easily bending and deforming the distal end side in U-shape, the rotation transmission performance for making the guide wire pass through the occlusion of the blood vessel, and the fatigue resistance for using repeatedly can be improved. These performances are important technical problems for making the guide wire reach the vascular lesion rapidly and improving the passability through the occlusion of the blood vessel.

The present invention provides a guide wire capable of treating the vascular lesion rapidly and significantly improving passability at the vascular lesion.

The guide wire of the present invention includes a core having a portion gradually tapered in diameter from a proximal end side to a distal end side, and a distal end portion of the core is inserted into an outer coil so that the distal end portion passes through the outer coil. The distal end portion of the core has a distal small-diameter body and a combined truncated cone in order from the distal end side to the proximal end side. A distal end (outer coil distal end) of the outer coil is connected with a distal end (core distal end) of the distal small-diameter body to form a distal joining section. A proximal end (outer coil proximal end) of the outer coil is connected with a proximal end (core proximal end) of the distal end portion of the core to form an outer coil proximal joining section.

The combined truncated cone is formed by longitudinally connecting at least two truncated cones. A longitudinal length of each of the truncated cones is reduced in order from the proximal end side to the distal end side. An outer diameter ratio between a maximum outer diameter of the core proximal end and a minimum outer diameter of the core distal end in each of the truncated cones is increased in order from the proximal end side to the distal end side. (The outer diameter ratio is calculated by dividing the maximum outer diameter of the core proximal end by the minimum outer diameter of the core distal end.)

When a maximum outer diameter of the combined truncated cone is defined as D0, a minimum outer diameter of the combined truncated cone is defined as D1, a total length of the combined truncated cone is defined as L, and an outer diameter at an arbitrary position X, which is located from a center in a cross section of the maximum outer diameter D0 to the core distal end of the combined truncated cone, is defined as Dm, and the arbitrary position X is within a range of 0<X<L, the outer diameter Dm of the combined truncated cone satisfies the following relational expression:

$$Dm > \{D0 - (D0 - D1)X/L\}.$$

When the truncated cone located at the most distal end in the combined truncated cone is defined as a first truncated cone, a twist angle of the first truncated cone is defined as $\theta o$, and a twist angle of the distal small-diameter body is defined as $\theta 1$, a twist angle ratio ($\theta 1/\theta o$) between the twist angle $\theta 1$ of the distal small-diameter body and the twist angle $\theta o$ of the first truncated cone is greater than 1.

The distal small-diameter body has a rectangular cross-sectional shape having an aspect ratio of equal to or greater than 1.676 and equal to or smaller than 3.958, the aspect ratio being calculated by dividing a long side by a short side. The twist angle ratio ($\theta 1/\theta o$) between the twist angle $\theta 1$ of the distal small-diameter body and the twist angle $\theta o$ of the first truncated cone is equal to or greater than 1.210 and equal to or smaller than 2.706.

The outer coil includes a large diameter proximal portion and a small diameter distal portion in order from the proximal end side to the distal end side. When an outer diameter of the large diameter proximal portion of the outer coil is defined as B1, an outer diameter of the small diameter distal portion of the outer coil is defined as B2, and a maximum outer diameter of the core proximal end of the first truncated cone is defined as D2, since the minimum outer diameter of the core distal end of the first truncated cone is D1, an outer diameter ratio (D2/D1) between the maximum outer diameter D2 of the core proximal end and the minimum outer diameter D1 of the core distal end in the first truncated cone is greater than an outer diameter ratio (B1/B2) of the outer coil satisfying the following relational expression: {(D2/D1)>(B1/B2)}.

An inner coil has a large diameter proximal portion (inner coil large diameter proximal portion) and a small diameter distal portion (inner coil small diameter distal portion) in order from the proximal end side to the distal end side.

The inner coil is arranged concentrically with the outer coil on an outside of the distal end portion of the core and an inside of the outer coil so that a longitudinal length of the inner coil is shorter than the longitudinal length of the outer coil. The outer coil distal end of the outer coil, an inner coil distal end of the inner coil (distal end of the small diameter distal portion), and the core distal end of the distal small-diameter body are connected with each other to form the distal joining section. An inner coil proximal end (proximal end of the inner coil large diameter proximal portion) is connected with the distal end portion of the core to form an inner coil proximal joining section.

The combined truncated cone is formed by the first truncated cone and a second truncated cone in order from the distal end side to the proximal end side. At least a part of the first truncated cone is arranged inside the inner coil. When a maximum outer diameter of the proximal end of the second truncated cone is defined as D0, the minimum outer diameter of the distal end of the second truncated cone is defined as D2, an outer diameter of the inner coil large diameter proximal portion is defined as A1, and an outer diameter of the inner coil small diameter distal portion is defined as A2, an outer diameter ratio (D2/D1) of the first truncated cone is greater than an outer diameter ratio (D0/D2) of the second truncated cone satisfying the following relation: {(D2/D1)>(D0/D2)}, and the outer diameter ratio (D2/D1) of the first truncated cone, the outer diameter ratio (A1/A2) of the inner coil, and the outer diameter ratio (B1/B2) of the outer coil satisfy the following relation: (D2/D1)>(A1/A2)>(B1/B2).

A roughly wound part is formed on the outer coil arranged on an outside of a boundary section between the distal end portion of the first truncated cone and the proximal end of the distal small-diameter body or on both the outer coil and the inner coil so that a length of the roughly wound part is at least 5 mm in the longitudinal direction, the length being calculated by adding the distal end side and the proximal end side of the boundary section.

In the medical guide wire of the present invention, the distal end portion of the core inserted into the outer coil has a distal small-diameter body and a combined truncated cone formed by connecting at least two truncated cones in order from the distal end side to the proximal end side, and when the truncated cone located at the most distal end in the combined truncated cone is defined as a first truncated cone, a twist angle of the first truncated cone is defined as $\theta o$, and a twist angle of the distal small-diameter body is defined as $\theta 1$, a twist angle ratio ($\theta 1/\theta o$) between the twist angle $\theta 1$ of the distal small-diameter body and the twist angle $\theta o$ of the first truncated cone is greater than 1. When the twist angle $\theta 1$ of the distal small-diameter body located at the distal end side is specified to be greater than the twist angle $\theta o$ of the first truncated cone located at the proximal end side, the flexibility for bending in U-shape at the distal small-diameter body side can be increased. When the structure of the first truncated cone having an outer diameter gradually increased from the distal end side to the proximal end side (or from the proximal end side to the distal end side) is used, the twist angle ratio ($\theta 1/\theta o$) can be increased compared to the case of the constant diameter because the diameter of the proximal end side is increased.

The combined truncated cone is formed by longitudinally connecting at least two truncated cones. A longitudinal length of each of the truncated cones is reduced in order from the proximal end side to the distal end side. An outer diameter ratio between a maximum outer diameter of the core proximal end and a minimum outer diameter of the core distal end in each of the truncated cones is increased in order from the proximal end side to the distal end side. (The outer diameter ratio is calculated by dividing the maximum outer diameter of the core proximal end by the minimum outer diameter of the core distal end.)

Outer diameters of the combined truncated cones satisfy a predetermined relational expression. When the outer diameter ratio of the first truncated cone located at the distal end is specified to be greater than the outer diameter ratio of the truncated cone located at the proximal end side, the twist angle $\theta o$ of the first truncated cone located at the distal end can be reduced for operating the proximal end side although the core having a small diameter is used.

The combined truncated cone including the first truncated cone is arranged at the proximal end of the distal small-diameter body.

When the structure of the combined truncated cone in which the truncated cones are connected on the proximal end of the first truncated cone is used, the twist angle ratio ($\theta 1/\theta o$) between the twist angle $\theta o$ of the first truncated cone and the twist angle $\theta 1$ of the distal small-diameter body can be further increased by reducing the twist angle $\theta o$. Thus, the flexibility for bending at the distal small-diameter body side can be further increased. From the above, the flexibility for bending in U-shape at the distal end can be increased and the distal end can be quickly reached to the entrance of the vascular lesion. In addition, by using the structure of the combined truncated cone, the rotation transmission performance of the distal end portion of the core toward the distal end side, the bending rigidity, the buckling strength, the fatigue resistance for using repeatedly and the passability at the vascular lesion can be further increased. Thus, the present invention can provide a guide wire greatly contributed to the treatment of the vascular lesion by being quickly reached to the vascular lesion and having high passability at the vascular lesion.

The distal small-diameter body has a rectangular cross-sectional shape having an aspect ratio of equal to or greater than 1.676 and equal to or smaller than 3.958. (The aspect ratio is calculated by dividing a long side by a short side.) The twist angle ratio ($\theta 1/\theta o$) between the twist angle $\theta 1$ of the distal small-diameter body and the twist angle θo of the first truncated cone is preferably equal to or greater than 1.210 and equal to or smaller than 2.706.

If the twist angle ratio (θ1/θo) between the twist angle θ1 of the distal small-diameter body and the twist angle θo of the first truncated cone is smaller than 1, the twist angle θ1 of the distal small-diameter body is smaller than the twist angle θo of the first truncated cone. In this case, the first truncated cone is more easily bent than the distal small-diameter body and it is difficult to keep the flexibility easily bending at the distal small-diameter body side.

If the twist angle ratio (θ1/θo) is greater than the above described upper limit value, the distal small-diameter body cannot be assembled with the outer coil because the length of the diagonal line of the long side and the short side of the rectangular cross-section of the distal small-diameter body is larger than the inner diameter of the outer coil as described later or the insertion operation is difficult in the bending and meandering blood vessel because the distal end becomes a meandering shape by being interfered or caught by the inner wall of the outer coil when the distal end is bent and deformed. Accordingly, the angle ratio (θ1/θo) is preferably within the above described range.

The outer coil includes a large diameter proximal portion and a small diameter distal portion in order from the proximal end side to the distal end side. When an outer diameter of the large diameter proximal portion of the outer coil is defined as B1, an outer diameter of the small diameter distal portion of the outer coil is defined as B2, and a maximum outer diameter of the core proximal end of the first truncated cone is defined as D2, an outer diameter ratio (D2/D1) between the maximum outer diameter D2 of the core proximal end and the minimum outer diameter D1 of the core distal end in the first truncated cone is greater than an outer diameter ratio (B1/B2) of the outer coil satisfying the following relational expression: {(D2/D1)>(B1/B2)}. When the outer coil is formed in the tapered shape, the rotation transmission performance from the proximal end side to the distal end side is improved. When the outer diameter ratio of the first truncated cone is specified to be larger than the outer diameter ratio of the outer coil, the torsional force applied on the distal end portion of the core by the combined truncated cone from the proximal end side to the distal end side is compensated. Thus, the twist angle ratio (θ1/θo) between the distal small-diameter body and the first truncated cone is increased. From the above, when the structure of the combined truncated cone of the distal end portion of the core and the taper shaped outer coil are simultaneously used, the bending rigidity, the buckling strength and other performance can be improved and the torsional moment toward the distal end side can be increased. Thus, the rotation transmission performance toward the distal end side can be further increased.

The outer coil and the inner coil have a large diameter proximal portion and a small diameter distal portion in order from the proximal end side to the distal end side. The inner coil is arranged concentrically with the outer coil on an outside of the distal end portion of the core and an inside of the outer coil so that a longitudinal length of the inner coil is shorter than the longitudinal length of the outer coil. The distal end (outer coil distal end) of the small diameter distal portion of the outer coil, the distal end (inner coil distal end) of the inner coil small diameter distal portion of the inner coil, and the distal end (core distal end) of the distal end portion of the core are connected with each other to form a distal joining section. The proximal end (inner coil proximal end) of the inner coil large diameter proximal portion of the inner coil is connected with the distal end portion of the core to form an inner coil proximal joining section.

The combined truncated cone is formed by the first truncated cone and a second truncated cone in order from the distal end side to the proximal end side. At least a part of the first truncated cone is arranged inside the inner coil. When a maximum outer diameter of the proximal end of the second truncated cone is defined as D0, the minimum outer diameter of the distal end of the second truncated cone is defined as D2, an outer diameter of the inner coil large diameter proximal portion is defined as A1, and an outer diameter of the inner coil small diameter distal portion is defined as A2, an outer diameter ratio (D2/D1) of the first truncated cone is greater than an outer diameter ratio (D0/D2) of the second truncated cone satisfying the following relation: {(D2/D1)>(D0/D2)}, and the outer diameter ratio (D2/D1) of the first truncated cone, the outer diameter ratio (A1/A2) of the inner coil, and the outer diameter ratio (B1/B2) of the outer coil satisfy the following relation: (D2/D1)>(A1/A2)>(B1/B2).

Because of the tapered shape of the inner coil and the outer coil, the rotation transmission performance from the proximal end side to the distal end side is further improved. When the outer diameter ratio of the first truncated cone is specified to be larger than the outer diameter ratio of the outer coil and the outer diameter ratio of the inner coil, the torsional force applied on the distal end portion of the core by the combined truncated cone from the proximal end side to the distal end side is further compensated. Thus, the twist angle ratio (θ1/θo) between the distal small-diameter body and the first truncated cone is further increased.

From the above, when the structure of the combined truncated cone of the distal end portion of the core and the taper shaped outer coil and inner coil are simultaneously used, the bending rigidity, the buckling strength and other performance can be further improved and the torsional moment toward the distal end side can be further increased. Thus, the rotation transmission performance toward the distal end side can be further increased.

A roughly wound part is formed on the outer coil arranged on an outside of a boundary section between the distal end portion of the first truncated cone and the proximal end of the distal small-diameter body or on both the outer coil and the inner coil so that a length of the roughly wound part is at least 5 mm in the longitudinal direction, the length being calculated by adding the distal end side and the proximal end side of the boundary section.

From the above, the flexibility for bending in U-shape at the distal end can be compensated at the boundary section between the first truncated cone and the distal small-diameter body while the twist angle ratio (θ1/θo) between the distal small-diameter body and the first truncated cone is increased.

DETAILED DESCRIPTION OF THE INVENTION

Embodiments

Hereafter, embodiments of a guide wire of the present invention will be explained.

Figure 1:
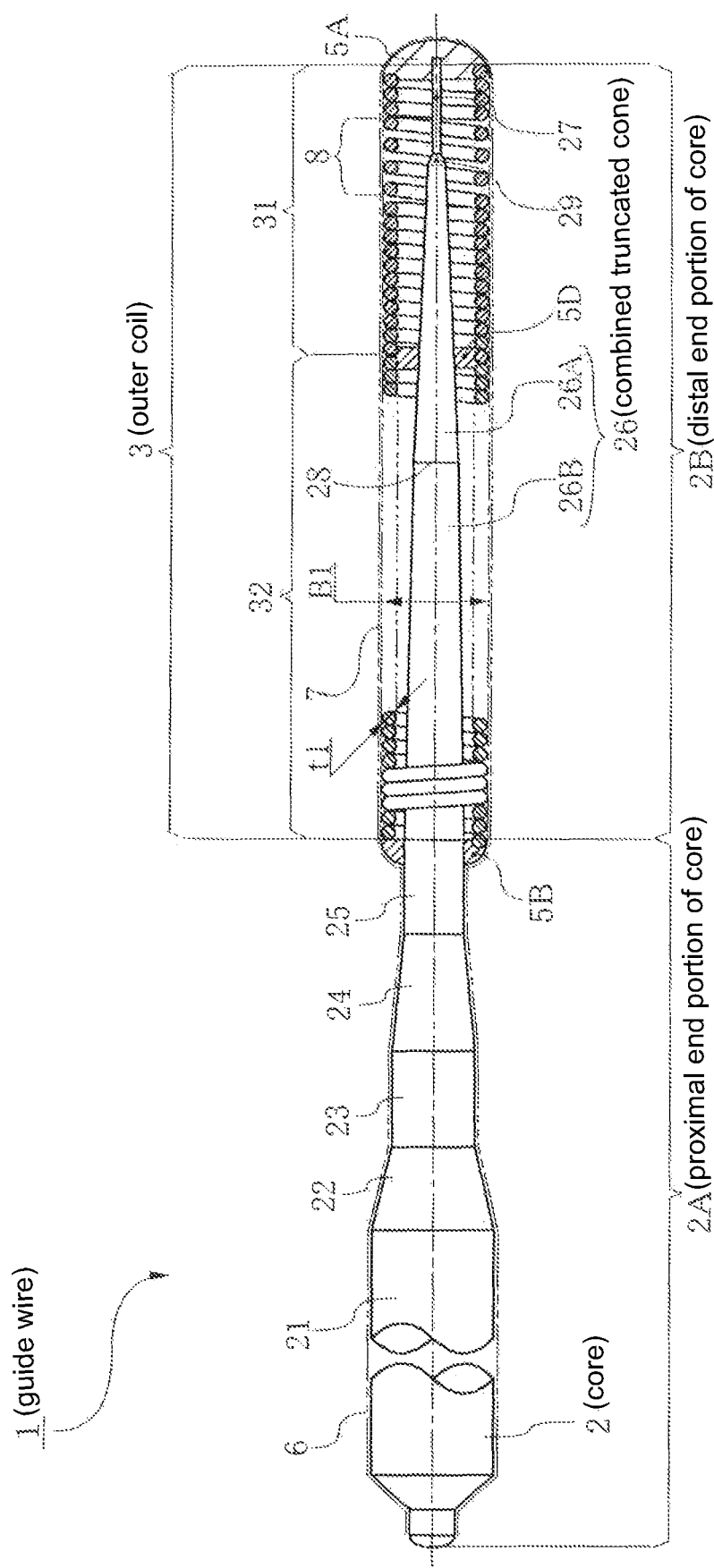
FIG. 1 is a partially cutaway side view showing whole a guide wire concerning the first embodiment of the present invention.
Figure 2:
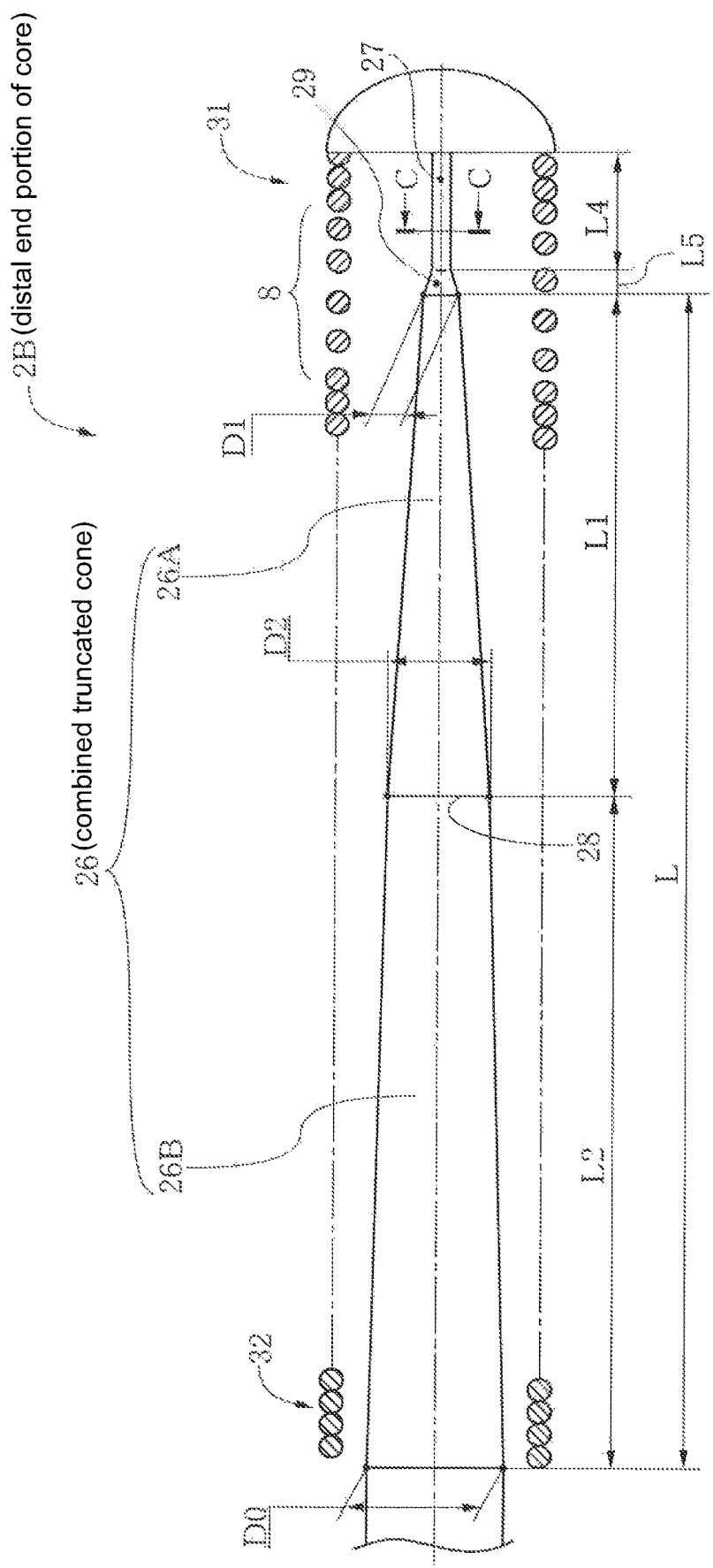
FIG. 2 is a partially cutaway side view showing a distal end portion having a distal small-diameter body and a combined truncated cone formed by combining two truncated cones.
Figure 3:
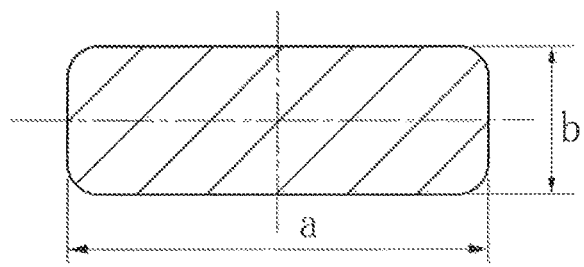
FIG. 3 is a cross-sectional view of the distal small-diameter body shown in FIG. 2.

FIGS. 1-3 show a guide wire 1 of the first embodiment of the present invention. FIG. 1 show an overall view, FIG. 2 shows a main part of the distal end portion, and FIG. 3 shows a cross-sectional view cut at a line C-C in FIG. 2.

The guide wire 1 includes a core 2, an outer coil 3, a fluorocarbon polymer coating 6, and a hydrophilic polymer coating 7. The core 2 includes a proximal end portion 2A of the core, a distal end portion 2B of the core, and a portion gradually tapered in diameter from the proximal end side to the distal end side.

The distal end portion 2B of the core passes through the outer coil 3. By using a bonding member, a distal end (outer coil distal end) of the outer coil 3 is connected with a distal end (core distal end) of the distal end portion 2B of the core to form a distal joining section 5A having a rounded shape at the tip, and a proximal end (outer coil proximal end) of the outer coil 3 is connected with a proximal end (core proximal end) of the distal end portion 2B of the core to form an outer coil proximal joining section 5B.

The fluorocarbon polymer coating 6 is formed on an outer periphery of the proximal end portion 2A of the core located at the proximal end side (large diameter side). The hydrophilic polymer coating 7 is formed on an outer periphery of the outer coil 3. Note that the guide wire 1 of the present invention has an extremely small diameter relative to its length. Therefore, the guide wire 1 is partially exaggerated or omitted in drawings because it is difficult to illustrate the guide wire 1 in a specified area if the same scaling is used for horizontal and vertical directions.

The core 2 is formed by a first constant diameter portion 21, a first tapered portion 22, a second constant diameter portion 23, a second tapered portion 24, a third constant diameter portion 25, a combined truncated cone 26 formed by connecting a first truncated cone 26A and a second truncated cone 26B, a boundary section 29, and a distal small-diameter body 27 in order from the proximal end side to the distal end side. The boundary section 29 is located between the first truncated cone 26A and the distal small-diameter body 27.

The outer diameter is gradually reduced from the first constant diameter portion 21 to the first truncated cone 26A in a range of 0.3556 mm (0.014 inch) to 0.054 mm. The distal small-diameter body 27 has a rectangular cross-sectional shape having an aspect ratio (a/b) between a long side "a" and a short side "b" of a predetermined range described later.

The outer diameter of the combined truncated cone 26 is gradually reduced from 0.180 mm at the proximal end (large diameter side) to 0.054 mm at the distal end (small diameter side). The outer coil proximal joining section 5B of the outer coil 3 is connected with the proximal end (large diameter side having a diameter of 0.180 mm) of the second truncated cone 26B by using a brazing material or other joining members. The outer coil proximal joining section 5B can be connected with the third constant diameter portion 25 having an outer diameter of 0.180 mm by using the joining members.

The core 2 is made from a stainless steel wire, a Ni—Ti alloy wire or the like. For example, as shown in Japanese Patent Laid-Open Publication No. H11-006037, a stainless steel wire having high strength manufactured by repeating a wire drawing process and an annealing process is used.

In addition, as shown in Japanese Patent Laid-Open Publication No. 2002-069555, a Ni—Ti alloy wire manufactured by thermal processing under certain conditions is used. An austenitic stainless steel wire having a tensile strength of 2200 MPa to 3500 MPa is preferably used.

This is because the tensile strength can be easily increased by a treatment of diameter reduction and wire drawing. In addition, a process of centerless grinding of the combined truncated cone 26 becomes easier although it will be described later. Note that the combined truncated cone 26 here means a structure of having a plurality of truncated cone shapes in the longitudinal direction manufactured by grinding a single wire. In addition, the core 2 can be also formed by welding and joining different kinds of wires between the distal end portion 2B and the proximal end portion 2A. For example, same as the combination of the material of the core, the proximal end portion 2A can be the stainless steel wire and the distal end portion 2B can be the Ni—Ti alloy wire.

The outer coil 3 is formed by winding one or a plurality of wires. The outer coil 3 has a constant outer diameter B1 of 0.330 mm and a longitudinal length of 160 mm. A wire diameter t1 of the coil wire is 0.060 mm. A first outer coil 31 located at the distal end side is made of a coil formed by winding a radiopaque wire including gold, platinum, nickel-containing gold or nickel-containing platinum, for example. The longitudinal length of the first outer coil 31 is 40 mm. The first outer coil 31 can be wound densely at the proximal end side and roughly wound at the distal end side. However, in order to compensate the flexibility at the side of the distal small-diameter body 27, it is preferred that a roughly wound part 8 is formed on the first outer coil 31 arranged on an outside of the boundary section 29 so that a length of the roughly wound part 8 is at least 5 mm in the longitudinal direction when the length is calculated by adding the distal end side and the proximal end side of the boundary section. Note that a distance between windings of the roughly wound part is 0.07 times to 1.90 times greater than the wire diameter t1. A second outer coil 32 located at the proximal end side is made of a radiolucent stainless steel wire. The longitudinal length of the second outer coil 32 is 120 mm. The second outer coil 32 is densely wound.

The first outer coil 31 and the second outer coil 32 are connected with each other at a middle joining section 5D by screw fitting of the coil wires and fixed by using a brazing material or other means. Instead of the screw fitting, the coil wires can be connected with each other by welding, for example. Note that an austenitic stainless steel wire having a tensile strength of 2200 MPa to 3500 MPa is preferably used for the material of the coil wire of the second outer coil 32. By doing so, the coil wire having high tensile strength is obtained and the coil wire can be densely wound. Thus, the fatigue resistance can be increased by high torsional stress and high initial tension. The outer coil 3 can be formed by using one or a plurality of radiopaque wires including gold, platinum, nickel-containing gold or nickel-containing platinum, for example.

FIG. 2 shows a distal end portion 2B of the core having a distal small-diameter body 27 and a combined truncated cone 26 formed by combining two truncated cones. FIG. 3 shows a cross-sectional view of the distal small-diameter body 27 shown in FIG. 2.

Figure 4:
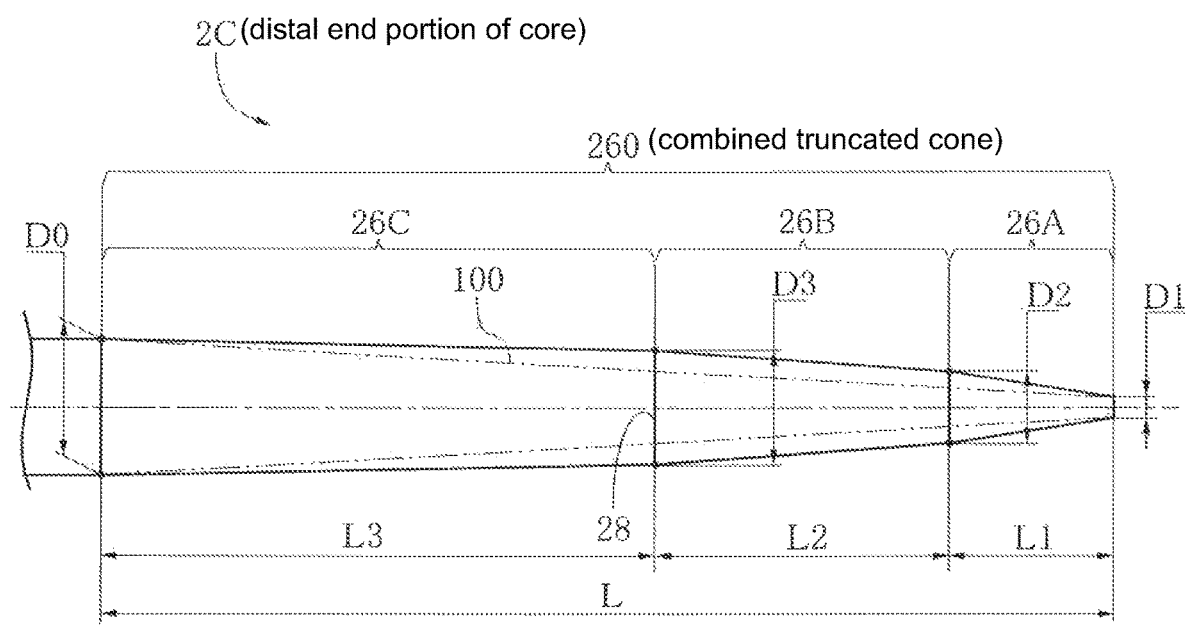
FIG. 4 is a side view showing a combined truncated cone formed by three truncated cones concerning the second embodiment.

FIG. 4 shows a distal end portion 2C of the core of the combined truncated cone formed by three truncated cones concerning the second embodiment. Except for the distal end portion 2C of the core, other specifications of the second embodiment are same as the first embodiment. Therefore, the same reference numerals are used for the same components. In FIG. 4, the distal small-diameter body 27 and the boundary section 29 shown in FIG. 2 are omitted.

In FIG. 2, the distal end portion 2B of the core is formed by the distal small-diameter body 27 and the combined truncated cone 26 in order from the distal end side to proximal end side. In addition, the boundary section 29 having a longitudinal length of 2 mm or less is formed between the distal small-diameter body 27 and the combined truncated cone 26. The boundary section 29 is a portion transferring from the combined truncated cone 26 to the distal small-diameter body 27 or from the distal small-diameter body 27 to the combined truncated cone 26. A longitudinal length L4 of the distal small-diameter body 27 is 12 mm. As shown in FIG. 3, the distal small-diameter body 27 has a rectangular cross-sectional shape. An aspect ratio (a/b) calculated by dividing a length "a" of a long side by a length "b" of a short side will be explained later. Note that the distal small-diameter body 27 of the first embodiment is formed to be a rectangular cross-section by pressing a wire material having a circular cross-section and an outer diameter of 0.054 mm. (This outer diameter is same as the outer diameter 0.054 mm of the minimum outer diameter D1 of the first truncated cone 26A.) The rectangular shape can be also formed by mechanical processing such as cutting. Here, the boundary section 29 means a portion transferring from the minimum outer diameter D1 of the first truncated cone to the distal small-diameter body 27 of the distal end side.

The combined truncated cone 26 is formed by two truncated cones: one is the second truncated cone 26B and the other is the first truncated cone 26B. In the second truncated cone 26B, the longitudinal length L2 is 100 mm, the maximum outer diameter D0 is 0.180 mm, and the minimum outer diameter D2 is 0.120 mm. In the first truncated cone 26A, the longitudinal length L1 is 40 mm, the maximum outer diameter D2 is 0.120 mm, and the minimum outer diameter D1 is 0.054 mm.

The longitudinal length L2 of the second truncated cone 26B is 100 mm, the longitudinal length L1 of the first truncated cone 26A is 40 mm, thus the longitudinal length is reduced from the proximal end side to the distal end side (L2>L1). The outer diameter ratio D0/D2 of the second truncated cone 26B is 1.50, the outer diameter ratio D2/D1 of the first truncated cone 26A is approximately 2.22, thus the outer diameter ratio is increased from the proximal end side to the distal end side {(D0/D2)<(D2/D1)}.

Next, a twist angle ratio (θ1/θo) between a twist angle θ1 of the distal small-diameter body 27 and a twist angle θo of the first truncated cone will be explained.

The longitudinal direction L4 of the distal small-diameter body 27 is 12 mm, and the distal small-diameter body 27a is formed to be a rectangular cross-sectional shape having an aspect ratio (a/b) of an approximately 1.868 between a length (0.0654 mm) of a long side "a" and a length (0.035 mm) of a short side "b" (FIG. 3).

In the distal small-diameter body 27 having a rectangular cross-sectional shape, when a torsional moment is defined as M, a length is defined as L4, a coefficient determined by the aspect ratio (a/b) between the length of the long side "a" and the length of the short side "b" is defined as k, a transverse elastic coefficient is defined as G, and a twist angle is defined as θ1 (rad), the twist angle θ1 (rad) of the distal small-diameter body 27 can be calculated from the following relational expression (1).

$$\theta 1 = M \times L4/(k \times a \times b^3 \times G) \quad (1)$$

The coefficient determined by the aspect ratio (a/b) can be calculated from the following relational expression (2).

$$k \approx 1/3 - 0.2 \times (b/a) \times \{1 - b^4/(12 \times a^4)\} \quad (2)$$

In the first truncated cone 26A, when a torsional moment is defined as M, a longitudinal length is defined as L1, a maximum outer diameter is defined as D2, a minimum outer diameter is defined as D1, a transverse elastic coefficient is defined as G, and a twist angle is defined as θ1 (rad), the twist angle θo (rad) of the first truncated cone 26A can be calculated from the following relational expression (3).

$$\theta o = 32 \times M \times L1 \times N1/(3\pi \times G \times N2) \quad (3)$$

However, the following relational expressions are satisfied.

$$N1 = D1^2 + D1 \times D2 + D2^2, N2 = D1^3 \times D2^3$$

The twist angle ratio (θ1/θo) between the twist angle θ1 (rad) of the distal small-diameter body 27 and the twist angle θo (rad) of the first truncated cone 26A can be calculated from the following relational expression (4).

$$\theta 1/\theta o = 3\pi \times N2 \times L4/(32 \times k \times a \times b^3 \times N1 \times L1) \quad (4)$$

However, the following relational expressions are satisfied.

$$N1 = D1^2 + D1 \times D2 + D2^2, N2 = D1^3 \times D2^3$$

Here, the longitudinal length L4 of the distal small-diameter body 27 is 12 mm, the length of the long side "a" is 0.0654 mm and the length of the short side "b" is 0.035 mm, and the longitudinal length L1 of the first truncated cone 26A is 40 mm, the maximum outer diameter D2 is 0.120 mm and the minimum outer diameter D1 is 0.054 mm. When these values are substituted in the relational expression (4), the twist angle ratio (θ1/θo) between the twist angle θ1 (rad) of the distal small-diameter body 27 and the twist angle θo (rad) of the first truncated cone 26A is approximately 1.586.

This indicates that the twist angle θ1 (rad) of the distal small-diameter body 27 is approximately 1.586 times larger than the twist angle θo (rad) of the first truncated cone 26A. Accordingly, when the proximal side is rotated, the distal small-diameter body 27 side is more easily twisted and deformed than the first truncated cone 26A. Thus, the distal end can be bent and deformed in U-shape.

From many experiments, the inventors found the lower limit value for obtaining the flexibility capable of being bent in U-shape at the distal small-diameter body 27 side and the upper limit value considering clearance and dimensions not to interfere with the inner diameter of the outer coil 3 and the length of a diagonal line of the long side "a" and short side "b" of the rectangular cross-section of the distal small-diameter body 27 when bent and deformed in U-shape. As a result, the upper/lower limit values of the aspect ratio (a/b) in the rectangular cross-section of the distal small-diameter body 27 is equal to or greater than 1.676 and equal to or smaller than 3.958.

Based on the above described range of the upper/lower limit values of the aspect ratio (a/b), the twist angle ratio ($\theta 1/\theta o$) between the twist angle $\theta 1$ (rad) of the distal small-diameter body 27 and the twist angle $\theta o$ (rad) of the first truncated cone 26A is equal to or greater than 1.210 and equal to or smaller than 2.706.

In the first embodiment of the present invention, the aspect ratio (a/b) in the rectangular cross-section of the distal small-diameter body 27 is approximately 1.869 and the twist angle ratio ($\theta 1/\theta o$) between the twist angle $\theta 1$ (rad) of the distal small-diameter body 27 and the twist angle $\theta o$ (rad) of the first truncated cone 26A is approximately 1.586. Thus, these values are within the range of the above described upper/lower limit values of the twist angle ratio ($\theta 1/\theta o$).

If the twist angle ratio ($\theta 1/\theta o$) between the twist angle $\theta 1$ (rad) of the distal small-diameter body 27 and the twist angle $\theta o$ (rad) of the first truncated cone 26A is smaller than 1, the twist angle $\theta 1$ (rad) of the distal small-diameter body 27 is less than the twist angle $\theta o$ (rad) of the first truncated cone 26A. Thus, the first truncated cone 26A is more easily bent than the distal small-diameter body 27. If the first truncated cone 26A is more easily bent than the distal small-diameter body 27, a length from a bending position to the distal joining section 5A is longer than the length of the distal small-diameter body 27. In this case, it is difficult to restore the original shape at the proximal side of the entrance of the vascular lesion of a peripheral blood vessel because a blood vessel diameter is small. Accordingly, the flexibility for easily bending at the distal small-diameter body 27 should be ensured. The lower limit value of the twist angle ratio ($\theta 1/\theta o$) is preferably 1.210.

If the twist angle ratio ($\theta 1/\theta o$) is greater than the above described upper limit value, the distal small-diameter body 27 cannot be assembled with the outer coil 3 because the length of the diagonal line of the long side "a" and short side "b" of the rectangular cross-section of the distal small-diameter body 27 is larger than the inner diameter of the outer coil 3 or the insertion operation cannot be performed in the bending and meandering blood vessel because the distal end becomes a meandering shape by being interfered or caught by the inner wall of the outer coil 3 when the distal end is bent and deformed.

In order to prevent the above described problems, the clearance and dimensions not to interfere with the inner diameter of the outer coil 3 and the length of a diagonal line of the rectangular cross-section of the distal small-diameter body 27 are found from many experiments.

Consequently, the twist angle ratio ($\theta 1/\theta o$) between the twist angle $\theta 1$ (rad) of the distal small-diameter body 27 and the twist angle $\theta o$ (rad) of the first truncated cone 26A is preferably equal to or greater than 1.210 and equal to or smaller than 2.706 as described above.

More preferably, the aspect ratio (a/b) of the rectangular cross-section of the distal small-diameter body 27 is equal to or greater than 1.778 and equal to or smaller than 3.680, the twist angle ratio ($\theta 1/\theta o$) is equal to or greater than 1.525 and equal to or smaller than 2.706.

From the above, the flexibility for twisting at the distal small-diameter body 27 side to form the U-shape can be further improved.

Although the distal small-diameter body 27 having a rectangular cross-section and the first truncated cone 26A having a diameter is gradually increase from the distal end side to the proximal end side are described in the first embodiment, the same explanation can be applied to a distal small-diameter body 27A having a circular cross-section. For the convenience of explanation, the reference numeral 27A is used for the distal small-diameter body having a circular cross-section.

In the distal small-diameter body 27A having a circular cross-section, when an outer diameter is defined as d, a longitudinal length is defined as L6, a torsional moment is defined as M, and a transverse elastic coefficient is defined as G, a cross sectional-second polar moment Ip can be shown as $(\pi/32) \times d^4$. Thus, the twist angle $\theta 2$ (rad) of the distal small-diameter body 27A can be calculated from the following relational expression (5).

$$\theta 2 = 32 \times M \times L6 / (\pi \times G \times d^4) \tag{5}$$

The twist angle ratio ($\theta 2/\theta o$) between the twist angle $\theta 2$ (rad) of the distal small-diameter body 27A and the twist angle $\theta o$ (rad) of the first truncated cone 26A can be calculated from the following relational expression (6).

$$\theta 2/\theta o = 3 \times L6 \times N2 / (d^4 \times L1 \times N1) \tag{6}$$

However, the following relational expressions are satisfied.

$$N1 = D1^2 + D1 \times D2 + D2^2, N2 = D1^3 \times D2^3$$

The twist angle ratio ($\theta 2/\theta o$) should be greater than 1 in order to specify the twist angle $\theta 2$ (rad) of the distal small-diameter body 27A having a circular cross-section to be larger than the twist angle $\theta o$ (rad) of the first truncated cone 26A.

When the outer diameter of the distal small-diameter body 27A having a circular cross-section is same as the minimum outer diameter D1 (D1=0.054 mm) of the first truncated cone 26A, the longitudinal length L6 of the distal small-diameter body 27A calculated from the relational expression (6) should be approximately 9.915 mm in order to specify the twist angle ratio ($\theta 2/\theta o$) between the twist angle $\theta 2$ (rad) of the distal small-diameter body 27A and the twist angle $\theta o$ (rad) of the first truncated cone 26A to be larger than 1.

Accordingly, the longitudinal length L6 should be greater than 9.915 mm in order to specify the twist angle $\theta 2$ (rad) of the distal small-diameter body 27A having a circular diameter and having the outer diameter same as the minimum outer diameter D1 (D1=0.054 mm) of the first truncated cone 26A to be greater than the twist angle $\theta o$ (rad) of the first truncated cone 26A.

When the twist angle ratio ($\theta 1/\theta o$) between the twist angle $\theta 1$ (rad) of the distal small-diameter body 27 having a rectangular cross-section and the twist angle $\theta o$ (rad) of the first truncated cone 26A is same as the first embodiment {twist angle ratio ($\theta 1/\theta o$) is approximately 1.586}, the longitudinal length L6 of the distal small-diameter body 27A having a circular cross-section calculated from the relational expression (6) is approximately 15.725. Thus, the longitudinal length L6 exceeds 9.915 mm, and exceeds the length L4 (12 mm) of the distal small-diameter body 27 having a rectangular cross-section.

As explained above, the present invention can be applied to the distal small-diameter body 27A having a circular cross-section if the longitudinal length L6 is specified to be longer than the length L4 (12 mm) of the distal small-diameter body 27 having a rectangular cross-section. Thus, the distal small-diameter body 27A is included in the present invention.

In order to shorten the longitudinal length of the distal small-diameter body 27A, the distal small-diameter body 27 having a rectangular cross-section is preferably used for the distal small-diameter body. (In the previous embodiment, the longitudinal length can be shortened 3.725 mm.) In order to obtain smooth rotational performance in the radial direction when rotating the proximal side, the distal small-diameter body 27A having a circular cross-section is preferably used for the distal small-diameter body. If the cross-sectional shape is rectangular, irregular rotation (stick-slip rotation) may be caused.

In FIG. 4, the distal end portion 2C of the core has a combined truncated cone 260 formed by connecting first to third truncated cones 26A, 26B and 26C. In the first truncated cone 26A, the longitudinal length is L1 (mm), the maximum outer diameter is D2 (mm), and the minimum outer diameter is D1 (mm). In the second truncated cone 26B, the longitudinal length is L2 (mm), the maximum outer diameter is D3 (mm), and the minimum outer diameter is D2 (mm). In a third truncated cone 26C, the longitudinal length is L3 (mm), the maximum outer diameter is D0 (mm), and the minimum outer diameter is D3 (mm). Note that the distal small-diameter body 27 and the boundary section 29 shown in FIG. 2 are omitted.

Each of the longitudinal lengths L1, L2 and L3 of the truncated cones 26A, 26B and 26C of the combined truncated cone 260 is reduced in order from the proximal end side to the distal end side (L3>L2>L1). Each of the outer diameter ratios (D2/D1), (D3/D2) and (D0/D3) of the truncated cones 26A, 26B and 26C is increased in order from the proximal end side to the distal end side {(D0/D3)<(D3/D2)<(D2/D1)}.

As explained above, in the distal end portions 2B, 2C of the core of the present invention, the combined truncated cones 26, 260 are formed by connecting at least one truncated cone on the proximal end side of the first truncated cone 26A so that at least two truncated cones including the first truncated cone 26A are longitudinally connected. The longitudinal length of each of the truncated cones is reduced in order from the proximal end side to the distal end side, i.e., from the first truncated cone 26C to the second truncated cone 26B, and further to the third truncated cone 26A. The outer diameter ratio between the maximum outer diameter of the proximal end and the minimum outer diameter of the distal end in each of the truncated cone is increased in order from the proximal end side to the distal end side. The outer diameter ratio is calculated by dividing the maximum outer diameter of the proximal end by the minimum outer diameter of the distal end.

By doing so, the outer diameter ratio of the first truncated cone 26A located at the distal end side becomes higher than the outer diameter ratio of the truncated cone located at the proximal end side. Thus, the twist angle θo (rad) of the first truncated cone 26A located at the distal end can be further reduced when the proximal end is operated while keeping the diameter small.

The combined truncated cones 26, 260 including the first truncated cone 26A are arranged at the proximal end of the distal small-diameter body 27. When the truncated cone is connected on the proximal end of the first truncated cone 26A to form the combined truncated cones 26, 260, the twist angle ratio (θ1/θo) between the twist angle θo (rad) of the first truncated cone 26A and the twist angle θ1 (rad) of the distal small-diameter body 27 can be further increased, while the twist angle θo (rad) is reduced. Thus, the flexibility for bending at the distal small-diameter body 27 side can be further increased.

Figure 5:
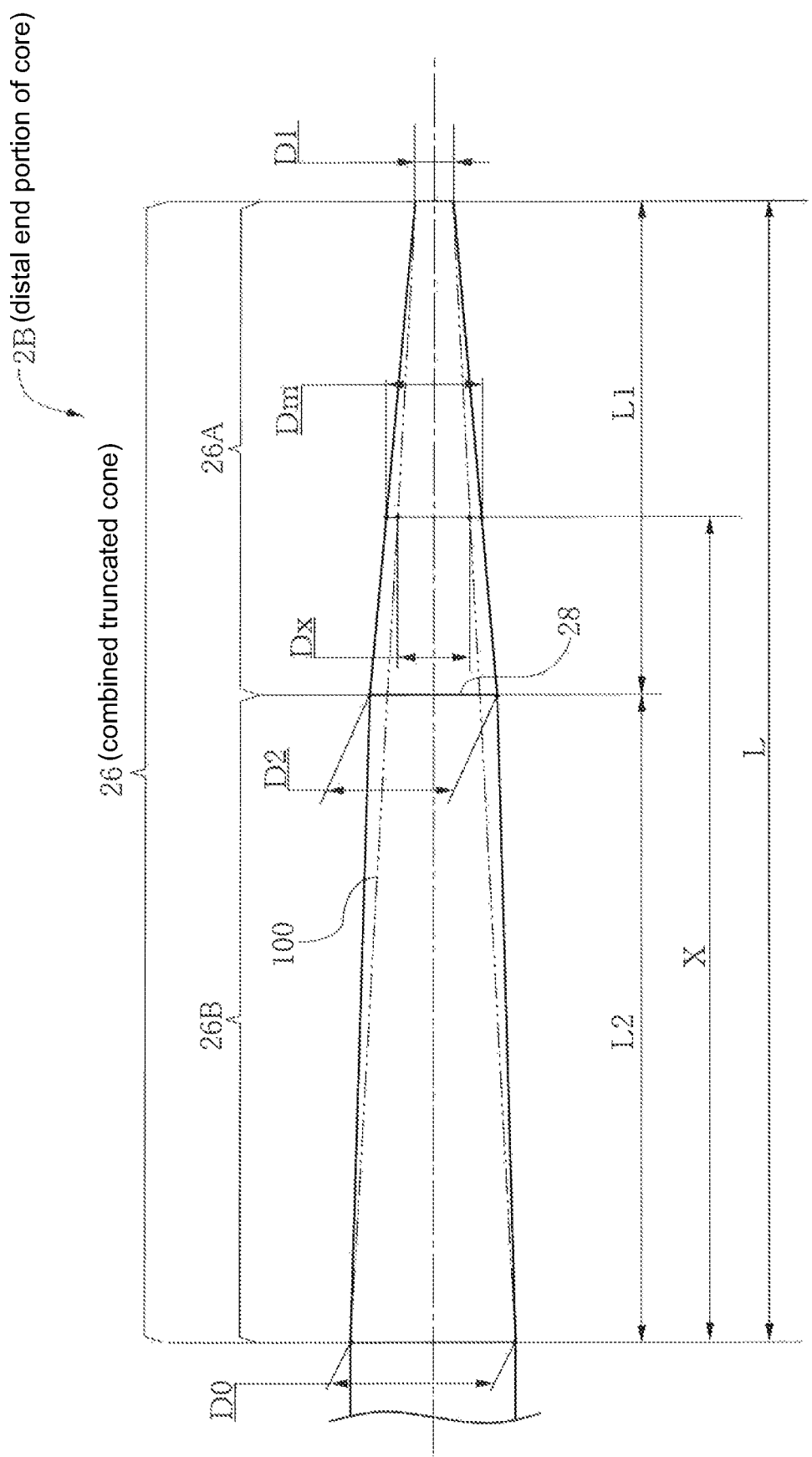
FIG. 5 is an explanation drawing showing a relational expression between an outer diameter ratio of the combined truncated cone formed by combining two truncated cones and an outer diameter of a virtual single truncated cone.

FIG. 5 is an explanation drawing showing a relational expression between the outer diameter ratio of the combined truncated cone 26 of the distal end portion 2B of the core of the present invention and an outer diameter of a virtual single truncated cone 100.

Solid lines indicate the combined truncated cone 26 formed by two truncated cones of the first embodiment of the present invention. Two-dot chain lines indicate the virtual single truncated cone 100 to explain the relational expression. Note that the distal small-diameter body 27 and the boundary section 29 are omitted.

In the combined truncated cone 26, the maximum outer diameter is D0 (mm), the minimum outer diameter is D1 (mm), and the total length is L (mm). When an arbitrary position of the combined truncated cone 26 is defined as X (mm), the arbitrary position X (mm) is located from a center in a cross section of the maximum outer diameter D0 (mm) to the distal end, the arbitrary position X (mm) is more than 0 mm and less than L mm (0<X<L), the outer diameter at the arbitrary position X (mm) is defined as Dm (mm), and the outer diameter of the virtual single truncated cone 100 is defined as Dx (mm), the outer diameter Dx (mm) satisfies the following relational expression (7).

$$Dx = D0 - (D0 - D1)X/L \quad (7)$$

Since the outer diameter Dm (mm) of the combined truncated cone 26 at the arbitrary position X (mm) is larger than the outer diameter Dx (mm) (Dm>Dx), the following relational expression (8) is satisfied.

$$Dm > \{D0 - (D0 - D1)X/L\} \quad (8)$$

The present invention is characterized in that the combined truncated cones 26, 260 including the first truncated cone 26A connected on the proximal end of the distal small-diameter body 27 satisfy the above described relational expression (8).

From the above, the twist angle ratio (θ1/θo) between the twist angle θo (rad) of the first truncated cone 26A and the twist angle θ1 (rad) of the distal small-diameter body 27 can be further increased. Thus, the flexibility for bending at the distal small-diameter body 27 side can be further increased.

More specially, the twist angle is reduced as the torsional rigidity increases, the torsional rigidity can be expressed by the product of a transverse elasticity modulus and a cross sectional-second polar moment, the cross sectional-second polar moment is higher in the structure of the combined truncated cones 26, 260 than the structure of the virtual single truncated cone 100 shown by two-dot chain lines in FIGS. 4 and 5, and the twist angle is reduced if the cross sectional-second polar moment increases. From the above, the reduction of the twist angle θo of the first truncated cone 26A is compensated and the twist angle ratio (θ1/θo) between the distal small-diameter body 27 and the first truncated cone 26A can be further increased.

Furthermore, when the proximal end side is pushed and pulled, the bending rigidity and the buckling strength of the combined truncated cones 26, 260 including the first truncated cone 26A can be increased.

This is because the bending rigidity can be expressed by the product of a longitudinal elastic modulus and the sectional secondary moment, and the sectional secondary moment is higher in the structure of the combined truncated cones 26, 260 than the structure of the single truncated cone 100. Since a compression stress is inversely proportional to a cross-sectional area, the compression stress is reduced as the cross-sectional area increases. In particular, in the combined truncated cones 26, 260, a joint portion 28, which is a portion from which the outer diameter of the core is significantly changed compared to the other portions, has a larger cross-sectional area than the corresponding area in the single truncated cone 100, and therefore the compression stress becomes low.

Therefore, when the guide wire is pushed and pulled in the longitudinal direction, because of the existence of the joint portion 28 having a larger cross-sectional area, the buckling strength can be increased in the structure of the combined truncated cones 26, 260 compared to the structure of the single truncated cone 100.

From the above, the distal end portions 2B, 2C of the core can be easily bent and deformed in U-shape at the distal end, and can be quickly reached to the entrance of the vascular lesion. Furthermore, by using the structure of the combined truncated cones 26, 260, the bending rigidity and the buckling strength of the distal end portions 2B, 2C of the core can be increased and the fatigue resistance for using repeatedly can be increased, and the passability at the vascular lesion can be further increased. Thus, the present invention can provide a guide wire greatly contributed to the treatment of the vascular lesion by being quickly reached to the vascular lesion and having high passability at the vascular lesion.

Figure 6:
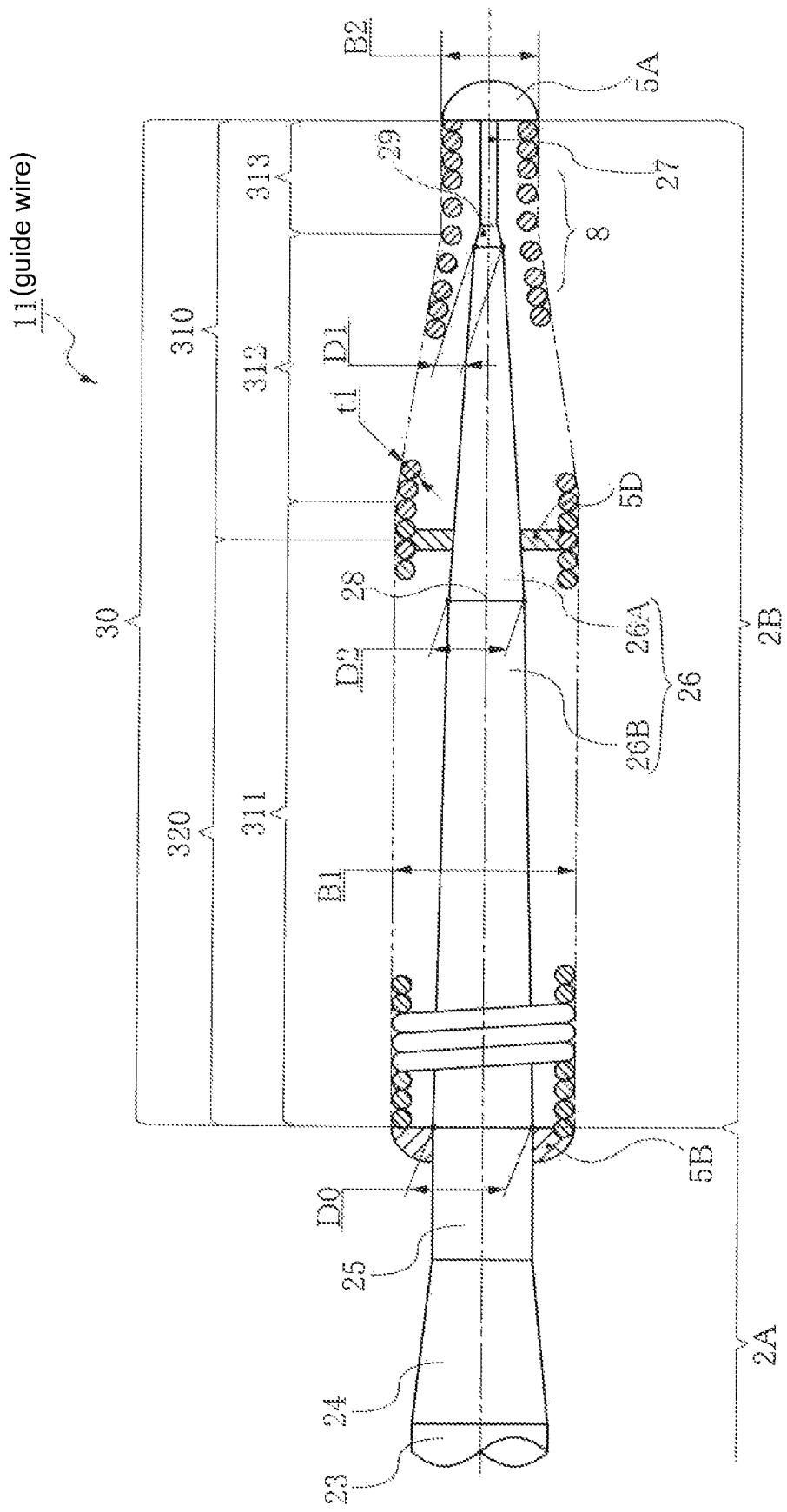
FIG. 6 is a partially cutaway side view showing a distal end portion of a guide wire concerning the third embodiment of the present invention.

FIG. 6 shows a guide wire 11 of the third embodiment. The guide wire 11 of the third embodiment is different from the guide wire 1 of the first embodiment in a point that an outer coil 30 is formed as a tapered shape from the proximal end side to the distal end side. Note that the fluorocarbon polymer coating 6 and the hydrophilic polymer coating 7 are omitted in the drawing.

In the outer coil 30, the outer diameter B1 of a large constant diameter proximal portion (large diameter proximal portion) 311 is 0.330 mm, the longitudinal length of the large constant diameter proximal portion 311 is 125 mm, the outer diameter of a tapered middle portion 312 is gradually reduced from 0.330 mm to 0.260 mm, the longitudinal length of the tapered middle portion 312 is 20 mm, the outer diameter B2 of a small constant diameter distal portion (small diameter distal portion) 313 is 0.260 mm, and the longitudinal length of the small constant diameter distal portion 313 is 15 mm.

The wire diameter t1 and the material of the coil wire are same as the first embodiment. A second outer coil 320 is made of a radiolucent wire and a first outer coil 310 is made of a radiopaque wire. The large constant diameter proximal portion (large diameter proximal portion) of the outer coil 30 is densely wound. The tapered middle portion of the outer coil 30 is densely wound at least at the proximal end side. The small constant diameter distal portion (small diameter distal portion) 313 of the outer coil 30 is roughly wound. Note that the small constant diameter distal portion (small diameter distal portion) 313 can be formed so that the proximal end side is densely wound and the distal end side is roughly wound. Same as the first embodiment, in order to increase the flexibility for bending at the distal small-diameter body 27 side, as shown in FIG. 6, a roughly wound part 8 is preferably formed on the small and constant diameter distal portion (small diameter distal portion) 313 of the first outer coil 310 arranged outside the boundary section 29 or on both the tapered middle portion 312 and the small and constant diameter distal portion (small diameter distal portion) 313 so that a length of the roughly wound part is at least 5 mm in the longitudinal direction when the length is calculated by adding the distal end side and the proximal end side of the boundary section 29.

When considering the outer diameter 0.3556 mm (0.0014 inch) of the guide wire used for the cardiovascular treatment, the outer diameter ratio B1/B2 between the outer diameter B1 of the large constant diameter proximal portion (large diameter proximal portion) 311 of the outer coil 30 and the outer diameter B2 of the small constant diameter distal portion (small diameter distal portion) 313 is 1.10 to 1.50. When considering the maximum outer diameter 0.4572 mm (0.018 inch) of the guide wire used for the lower extremity vessels, the outer diameter ratio B1/B2 is 1.10 to 1.80.

When considering both for the cardiovascular treatment and the lower extremity vessels, the outer diameter ratio B1/B2 is 1.10 to 1.80, and preferably 1.15 to 1.80. The outer diameter ratio B1/B2 of the outer coil 30 of the third embodiment is approximately 1.27.

The outer diameter ratio (D2/D1) between the maximum outer diameter D2 of the proximal end and the minimum outer diameter D1 of the distal end in the first truncated cone 26A located at the distal end in the combined truncated cone 26 is greater than the outer diameter ratio (B1/B2) of the outer coil 30 {(D2/D1)>(B1/B2)}. In the third embodiment, the outer diameter ratio B1/B2 of the outer coil 30 is approximately 1.27 and the outer diameter ratio D2/D1 of the first truncated cone 26A located at the distal end is approximately 2.22. Therefore, the outer diameter ratio D2/D1 of the first truncated cone 26A located at the distal end is greater than the outer diameter ratio B1/B2 of the outer coil {(D2/D1)>(B1/B2)}. When the outer coil 30 tapered toward the distal end side is used, the torsional force toward the distal end side of the distal end portion 2B of the core in the outer coil 30 can be compensated.

Since the outer diameter ratio D2/D1 between the proximal end and distal end of the first truncated cone 26A located at the distal end is larger than the outer diameter ratio B1/B2 of the outer coil 30, the torsional moment toward the distal end side can be increased and the twist angle ratio ($\theta1/\theta o$) between the twist angle $\theta o$ of the first truncated cone 26A and the distal small-diameter body $\theta 1$ can be increased. Furthermore, when the outer coil 30 having a tapered shape is simultaneously used, the rotation transmission performance toward the distal end side can be further improved.

Figure 7:
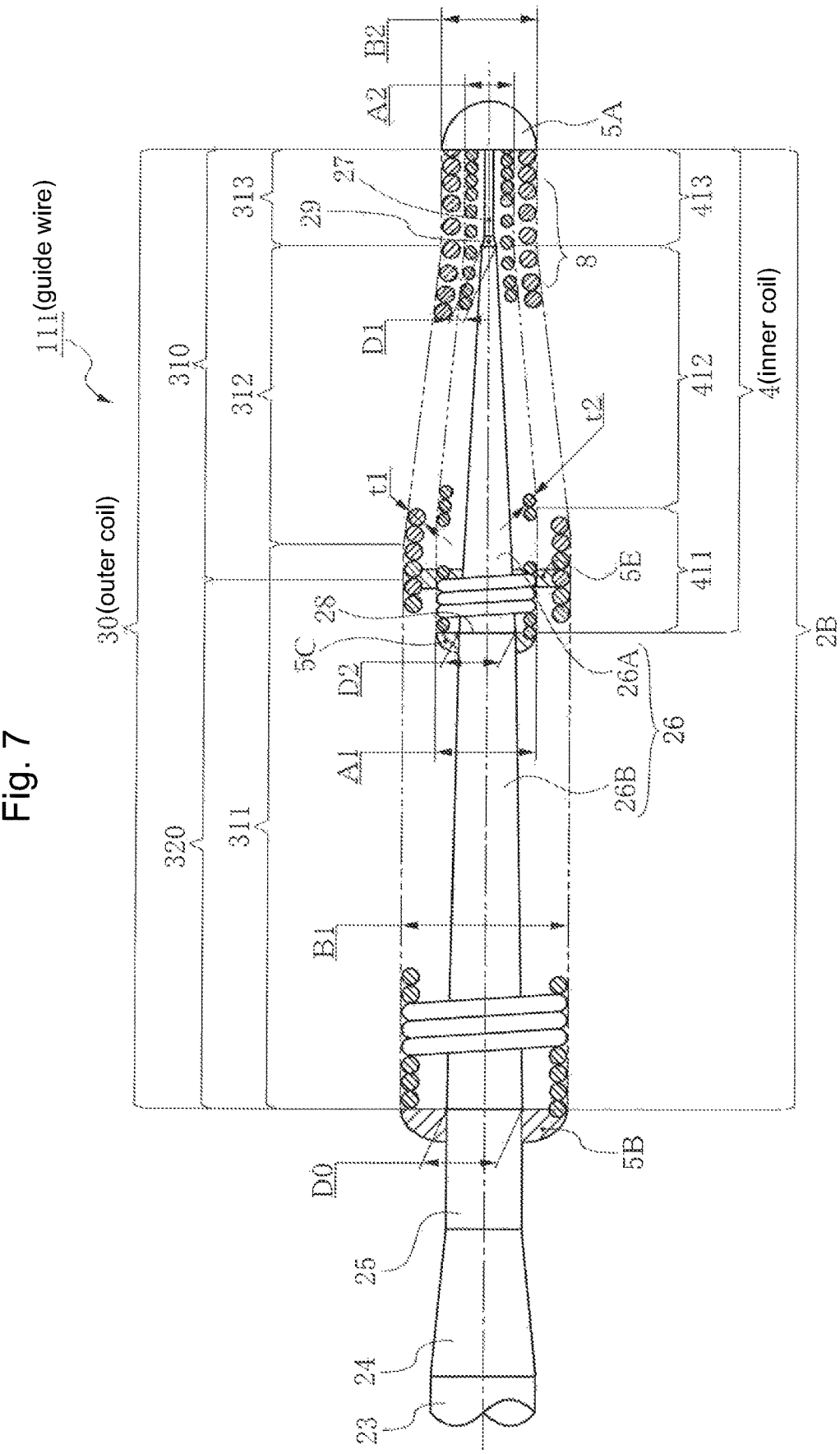
FIG. 7 is a partially cutaway side view showing a distal end portion of a guide wire concerning the fourth embodiment of the present invention.

FIG. 7 shows a guide wire 111 of the fourth embodiment. The guide wire 111 is different from the guide wire 11 of the third embodiment in a point that an inner coil 4 is provided inside the outer coil 30. The inner coil 4 has a smaller longitudinal length than the outer coil 30. The inner coil 4 is arranged concentrically with the outer coil 30. The inner coil has a tapered shape from the proximal end side to the distal end side. Note that the fluorocarbon polymer coating 6 and the hydrophilic polymer coating 7 are omitted in the drawing.

The distal end portion 2B of the core passes thorough the inner coil 4. The distal end (outer coil distal end) of the outer coil 30, the distal end (inner coil distal end) of the inner coil and the distal end (core distal end) of the distal end portion 2B of the core are connected with each other by using a bonding member or the like to form the distal joining section 5A having a rounded shape at the tip. The proximal end (inner coil proximal end) of the inner coil 4 is connected with the distal end portion 2B of the core to form an inner coil proximal joining section 5C. In a middle joining section 5E, the inner coil 4, the outer coil 30 and the distal end portion 2B of the core are integrally connected with each other. Note that the middle joining section 5E can be also formed by connecting only the inner coil 4 and the distal end portion 2B of the core or connecting only the inner coil 4 and the outer coil 30.

In the inner coil 4, the outer diameter A1 of a large constant diameter proximal portion (inner coil large diameter proximal portion) 411 is 0.185 mm, the longitudinal length of the large constant diameter proximal portion 411 is 20 mm, the outer diameter of a tapered middle portion 412 is gradually reduced from 0.185 mm at the proximal end side to 0.130 mm at the distal end side, and the longitudinal length of the tapered middle portion 412 is 20 mm, the outer diameter A2 of a small constant diameter distal portion (inner coil small diameter distal portion) 413 is 0.130 mm, the longitudinal length of the small constant diameter distal portion is 15 mm, and the wire diameter t2 of the coil wire is 0.030 mm. The inner coil 4 is formed by using one or a plurality of wires. In the above described structure, the large constant diameter proximal portion 411 is densely wound, the tapered middle portion 412 is densely wound at least at the proximal end side, and the small constant diameter distal portion 413 is roughly wound. In the small and constant diameter distal portion (inner coil small diameter distal portion) 313, the proximal end side can be densely wound while the distal end side is roughly wound. Same as the third embodiment, in order to increase the flexibility for bending at the distal small-diameter body 27 side, as shown in FIG. 7, a roughly wound part 8 is preferably formed on the small and constant diameter distal portions (small diameter distal portions) 313, 413 of the first outer coil 310 and the inner coil 4 arranged outside the boundary section 29 or on both the tapered middle portions 312, 412 and the small and constant diameter distal portions (small diameter distal portions) 313, 413 so that a length of the roughly wound part is at least 5 mm in the longitudinal direction when the length is calculated by adding the distal end side and the proximal end side of the boundary section 29.

When considering the outer diameter 0.3556 mm (0.0014 inch) of the guide wire used for the cardiovascular treatment, the outer diameter ratio A1/A2 between the outer diameter A1 of the large constant diameter proximal portion (inner coil large diameter proximal portion) 411 of the inner coil 4 and the outer diameter A2 of the small constant diameter distal portion (inner coil small diameter distal portion) 413 is 1.15 to 1.70. When considering the maximum outer diameter 0.4572 mm (0.018 inch) of the guide wire used for the lower extremity vessels, the outer diameter ratio A1/A2 is 1.15 to 2.80.

When considering both for the cardiovascular treatment and the lower extremity vessels, the outer diameter ratio A1/A2 is 1.15 to 2.80, preferably 1.15 to 2.75, and more preferably 1.25 to 2.75. The outer diameter ratio A1/A2 of the inner coil 4 of the fourth embodiment is approximately 1.42.

The outer diameter ratio (D2/D1) between the maximum outer diameter D2 of the proximal end and the minimum outer diameter D1 of the distal end in the first truncated cone 26A located at the distal end in the combined truncated cone 26 is greater than the outer diameter ratio D0/D2 of the second truncated cone 26B {(D2/D1)>(D0/D2)}. In addition, the outer diameter ratio D2/D1 of the first truncated cone 26A, the outer diameter ratio A1/A2 of the inner coil, and the outer diameter ratio B1/B2 of the outer coil satisfy the following relational expression (9).

$$(D2/D1) > (A1/A2) > (B1/B2) \quad (9)$$

In the fourth embodiment, the outer diameter ratio D2/D1 of the first truncated cone 26A is approximately 2.22 and the outer diameter ratio D0/D2 of the second truncated cone 26B is 1.50. Therefore, the outer diameter ratio D2/D1 of the first truncated cone 26A is greater than the outer diameter ratio D0/D2 of the second truncated cone 26B (approximately 2.22>1.50). In addition, the outer diameter ratio A1/A2 of the inner coil 4 is approximately 1.42 and the outer diameter ratio B1/B2 of the outer coil 30 is approximately 1.27. Therefore, the outer diameter ratio D2/D1 of the first truncated cone 26A, the outer diameter ratio A1/A2 of the inner coil 4, and the outer diameter ratio B1/B2 of the outer coil 30 are respectively approximately 2.22>approximately 1.42>approximately 1.27. Thus, the above described relational expression (9) is satisfied.

When the relational expression (9) is satisfied the torsional force from the proximal end side to the distal end side of the distal end portion 2B of the core by adopting the tapered shape for both the inner coil 4 and the outer coil 30 and increasing the outer diameter ratio from the outer coil 30 to the inner coil 4. Thus, the outer diameter ratio of the first truncated cone 26A is increased at the most and the twist angle of the first truncated cone 26A is further reduced. Accordingly, the twist angle ratio (θ1/θo) between the twist angle θo of the first truncated cone 26A and the twist angle θ1 of the distal small-diameter body 27 is further increased.

From the above, when the structure of the combined truncated cone 26 of the distal end portion 2B of the core and the taper shaped outer coil 30 and inner coil 4 are simultaneously used, the bending rigidity, the buckling strength and other performance can be further improved and the torsional moment toward the distal end side can be further increased. Thus, the rotation transmission performance toward the distal end side can be further increased.

The middle joining section 5E is preferably formed in a ring shape with a width of 0.22 mm to 1.5 mm by integrally connecting the proximal end side of the first truncated cone 26A, which is the large diameter side having a length of equal to or less than a half of the total length of the first truncated cone 26A, the large diameter side of the inner coil 4, which is the large diameter side having a length of equal to or less than a half of the total length of the inner coil 4, and the large diameter side of the outer coil 30 by using a bonding member such a brazing material.

It is preferred that the inner coil 4 and the outer coil 30 are densely wound at least from the proximal end to the middle joining section 5E.

Since the rotation transmission force toward the distal end side is proportional to the outer diameter ratio between the large diameter proximal portion and the small diameter distal portion (calculated by dividing the outer diameter of the large diameter proximal portion by the outer diameter of the small diameter distal portion), when the middle joining section 5E is formed by integrally connecting the proximal end side of the outer coil 30, the proximal end side of the inner coil 4 and the proximal end side of the first truncated cone 26A and coils are densely wound from the proximal end to the middle joining section 5E, the rotation force integrated by the tapered shape of the outer coil 30, the inner coil 4 and the first truncated cone 26A is transferred to the distal end side and the rotation transmission performance toward the distal end side can be further increased.

In the fourth embodiment, more preferably, the tapered middle portion 312 of the outer coil 30 and the tapered middle portion 412 of the inner coil 4 are arranged to be overlapped with each other, as shown in FIG. 7. When the tapered middle portions 312, 412 are coaxial and have an approximately same tapered shape at the overlapped position of the outer coil 30 and the inner coil 4, the rotation force transmitted from the large diameter side to the small diameter side of both the outer coil 30 and the inner coil 4 can be concentrated on the distal end side. Thus, the rotation transmission performance toward the distal end side can be more easily improved.

In the outer coils 3, 30 of the present invention, the distal end portion 2B of the core includes the distal small-diameter body 27 and the combined truncated cones 26, 260 in order from the distal end side to the proximal end side. Although the preferable number of the combined truncated cones is affected by the total length of the outer coils 3, 30, the number of the combined truncated cones is preferably at least two and equal to or less than 20 including the first truncated cone 26A when the total length of the outer coils 3, 30 is 20 mm to 350 mm.

In the explanation of the third embodiment and fourth embodiment, the shapes of the outer coil 30 and the inner coil 4 are formed by the large constant diameter proximal portions (large diameter proximal portions) 311, 411, the tapered middle portions 312, 412 and the small and constant diameter distal portions (small diameter distal portions) 313, 413 in order from the proximal end side to the distal end side. However, any shapes can be used as long as the large diameter proximal portion having a large diameter is provided on the proximal end side and the small diameter distal portion having a small diameter is provided on the distal end side.

Figure 8A:
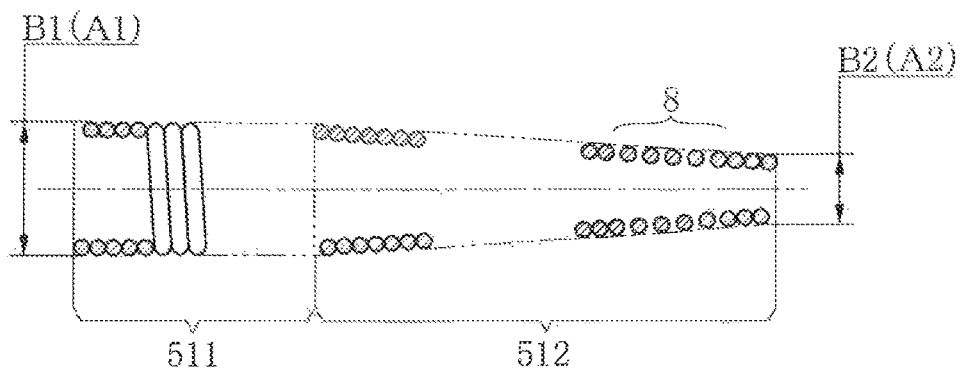
FIGS. 8A to 8C show other embodiments of an outer coil and an inner coil of the present invention.
Figure 8B:
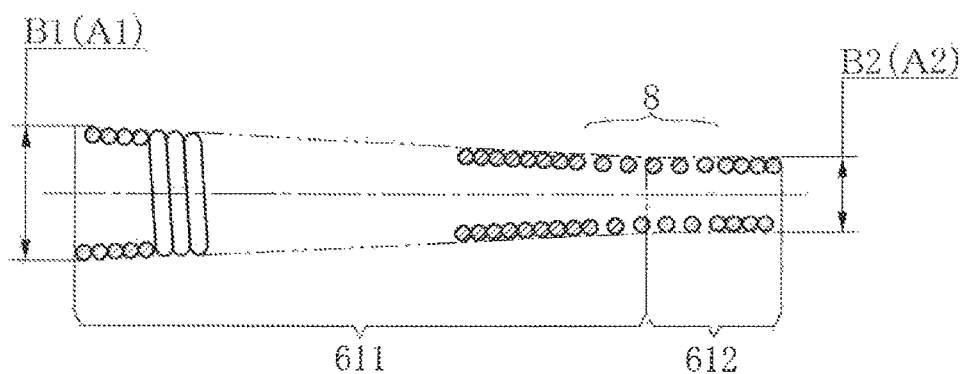
Figure 8C:
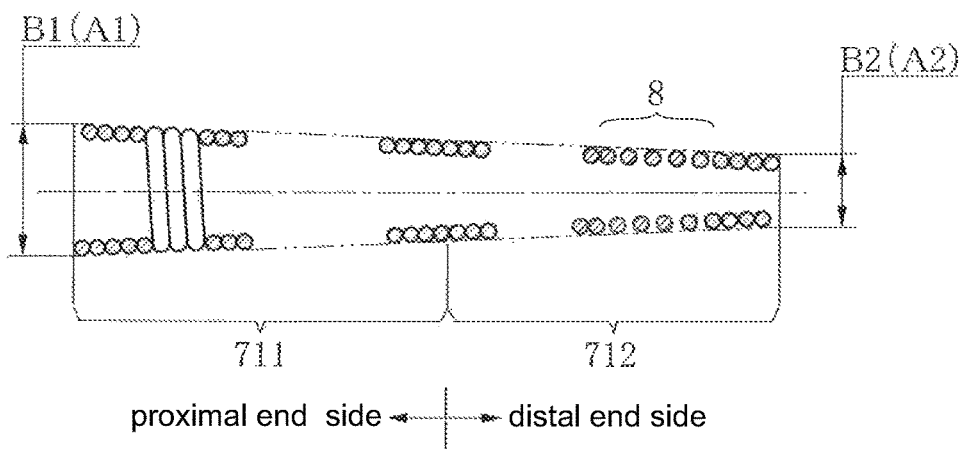

FIGS. 8A to 8C show other embodiments of the outer coil 30 and the inner coil 4. In FIG. 8A, a large diameter proximal portion 511 having a large constant outer diameter is provided on the proximal end side, and a small diameter distal portion 512 having an outer diameter gradually reducing toward the distal end side is provided on the distal end side. In FIG. 8B, a large diameter proximal portion 611 having an outer diameter gradually reducing from the proximal end side having a large diameter toward the distal end side is provided on the proximal end side, and a small diameter distal portion 612 having a small constant diameter is provided on the distal end side. In FIG. 8C, the outer diameter is gradually reduced from the proximal end side to the distal end side, and the coil is divided into two parts: a large diameter proximal portion 711 (a half in the total length) located on the proximal end side; and a small diameter distal portion 712 (the other half of the total length) located on the distal end side.

The outer coil 30 and the inner coil 4 can be formed by combining any shapes shown in FIGS. 8A to 8C or the shape described in the fourth embodiment. It is preferred that the outer coil 30 and the inner coil 4 have an approximately same tapered shape. In this case, the outer diameter ratio B1/B2 of the outer coil 30 is calculated by using the maximum outer diameter of the proximal end side as the outer diameter B1 of the large diameter proximal portion and using the maximum outer diameter of the distal end as the outer diameter B2 of the small diameter distal portion. Similarly, the outer diameter ratio A1/A2 of the inner coil 4 is calculated by using the maximum outer diameter of the proximal end side as the outer diameter A1 of the large diameter proximal portion and using the minimum outer diameter of the distal end side as the outer diameter A2 of the small diameter distal portion.

In the explanation of the above described embodiments 1 to 4, the distal end portion 2B of the core is formed by the distal small-diameter body 27 and the combined truncated cones 26, 260 including the first truncated cone 26A from the distal end side to the proximal end side. However, the present invention can be applied for the case that the distal end portion 2B of the core is formed by the distal small-diameter body 27 and only one truncated cone (the first truncated cone 26A) in order the distal end side to the proximal end side without using a plurality of truncated cones.

Namely, a medical guide wire of the present invention is comprised of a core that has a portion gradually tapered in diameter from a proximal end side to a distal end side; and an outer coil into which a distal end portion of the core is inserted, wherein the distal end portion of the core has a distal small-diameter body and a combined truncated cone in order from the distal end side to the proximal end side, an outer coil distal end of the outer coil is connected with a core distal end of the distal small-diameter body to form a distal joining section, an outer coil proximal end of the outer coil is connected with a core proximal end of the distal end portion of the core to form an outer coil proximal joining section, an outer diameter of the truncated cone is gradually increased from the distal end side to the proximal end side, when a twist angle of the first truncated cone is defined as $\theta o$ and a twist angle of the distal small-diameter body is defined as $\theta 1$, a twist angle ratio ($\theta 1/\theta o$) between the twist angle $\theta 1$ of the distal small-diameter body and the twist angle $\theta o$ of the first truncated cone is greater than 1.

In addition, the distal small-diameter body has a rectangular cross-sectional shape having an aspect ratio of equal to or greater than 1.676 and equal to or smaller than 3.958, the aspect ratio being calculated by dividing a long side by a short side, and the twist angle ratio ($\theta 1/\theta o$) between the twist angle $\theta 1$ of the distal small-diameter body and the twist angle $\theta o$ of the first truncated cone is equal to or greater than 1.210 and equal to or smaller than 2.706.

Furthermore, an outer diameter ratio (D2/D1) between the maximum outer diameter D2 and the minimum outer diameter D1 of the truncated cone is greater than an outer diameter ratio (B1/B2) of the outer coil 30 satisfying the following relational expression: {(D2/D1)>(B1/B2)}. Furthermore, the outer diameter ratio (B1/B2) of the outer coil 30 and the outer diameter ratio (A1/A2) of the inner coil 4 satisfy the following relation: (D2/D1)>(A1/A2)>(B1/B2).

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A medical guide wire, comprising:
   a core that has a portion gradually tapered in diameter from a proximal end side to a distal end side; and
   an outer coil into which a distal end portion of the core is inserted, wherein the distal end portion of the core has a distal small-diameter body and a combined truncated cone in order from the distal end side to the proximal end side, an outer coil distal end of the outer coil is connected with a core distal end of the distal small-diameter body to form a distal joining section, an outer coil proximal end of the outer coil is connected with a core proximal end of the distal end portion of the core to form an outer coil proximal joining section, the combined truncated cone is formed by longitudinally connecting at least two truncated cones, a longitudinal length of each of the truncated cones is reduced in order from the proximal end side to the distal end side, an outer diameter ratio between a maximum outer diameter of the core proximal end and a minimum outer diameter of the core distal end in each of the truncated cones is increased in order from the proximal end side to the distal end side, the outer diameter ratio is a ratio of the maximum outer diameter of the core proximal end with respect to the minimum outer diameter of the core distal end, when a maximum outer diameter of the combined truncated cone is defined as D0, a minimum outer diameter of the combined truncated cone is defined as D1, a total length of the combined truncated cone is defined as L, and an outer diameter Dm of the combined truncated cone at a position separated a distance X from a center in a cross section of the maximum outer diameter D0 to the core distal end of the combined truncated cone within a range of 0<X<L satisfies the following relational expression: Dm>{D0−(D0−D1)X/L}, and when a truncated cone located at the most distal end in the combined truncated cone is defined as a first truncated cone, a twist angle of the first truncated cone is defined as θo, and a twist angle of the distal small-diameter body is defined as θ1, a twist angle ratio (θ1/θo) between the twist angle θ1 of the distal small-diameter body and the twist angle θo of the first truncated cone is greater than 1, the twist angle θ1 being proportional to a longitudinal length of the distal small-diameter body and inversely proportional to a transverse elastic coefficient of the distal small-diameter body, the twist angle θo being proportional to a longitudinal length of the first truncated cone and inversely proportional to a transverse elastic coefficient of the first truncated cone.

2. The medical guide wire according to claim 1, wherein the distal small-diameter body has a rectangular cross-sectional shape having an aspect ratio of equal to or greater than 1.676 and equal to or smaller than 3.958, the aspect ratio being calculated by dividing a long side by a short side, and the twist angle ratio (θ1/θo) between the twist angle θ1 of the distal small-diameter body and the twist angle θo of the first truncated cone is equal to or greater than 1.210 and equal to or smaller than 2.706.

3. The medical guide wire according to claim 1, wherein the outer coil includes a large diameter proximal portion and a small diameter distal portion in order from the proximal end side to the distal end side, and when an outer diameter of the large diameter proximal portion of the outer coil is defined as B1, an outer diameter of the small diameter distal portion of the outer coil is defined as B2, and a maximum outer diameter of the core proximal end of the first truncated cone is defined as D2, since the minimum outer diameter of the core distal end of the first truncated cone is D1, an outer diameter ratio (D2/D1) between the maximum outer diameter D2 of the core proximal end and the minimum outer diameter D1 of the core distal end in the first truncated cone is greater than an outer diameter ratio (B1/B2) of the outer coil satisfying the following relational expression: {(D2/D1)>(B1/B2)}.

4. The medical guide wire according to claim 3, wherein an inner coil is arranged concentrically with the outer coil on an outside of the distal end portion of the core and an inside of the outer coil so that a longitudinal length of the inner coil is shorter than the longitudinal length of the outer coil, the inner coil having an inner coil large diameter proximal portion and an inner coil small diameter distal portion in order from the proximal end side to the distal end side, the outer coil distal end of the outer coil, an inner coil distal end of the inner coil, and the core distal end of the distal small-diameter body are connected with each other to form the distal joining section, an inner coil proximal end is connected with the distal end portion of the core to form an inner coil proximal joining section, the combined truncated cone is formed by the first truncated cone and a second truncated cone in order from the distal end side to the proximal end side, at least a part of the first truncated cone is arranged inside the inner coil, when a maximum outer diameter of a proximal end of the second truncated cone is defined as D0, a minimum outer diameter of a distal end of the second truncated cone is defined as D2, an outer diameter of the inner coil large diameter proximal portion is defined as A1, and an outer diameter of the inner coil small diameter distal portion is defined as A2, an outer diameter ratio (D2/D1) of the first truncated cone is greater than an outer diameter ratio (D0/D2) of the second truncated cone satisfying the following relation: {(D2/D1)>(D0/D2)}, and the outer diameter ratio (D2/D1) of the first truncated cone, the outer diameter ratio (A1/A2) of the inner coil, and the outer diameter ratio (B1/B2) of the outer coil satisfy the following relation: (D2/D1)>(A1/A2)>(B1/B2).

5. The medical guide wire according to claim 1, wherein a roughly wound part is formed on the outer coil arranged on an outside of a boundary section between the distal end portion of the first truncated cone and the proximal end of the distal small-diameter body or on both the outer coil and an inner coil so that a length of the roughly wound part is at least 5 mm in the longitudinal direction, the length being calculated by adding the distal end side and the proximal end side of the boundary section.

* * * * *